(12) United States Patent
Hara et al.

(10) Patent No.: US 6,269,681 B1
(45) Date of Patent: Aug. 7, 2001

(54) GROUP OF PARTICLES FOR AIR FILTER TEST AND METHOD OF AIR FILTER TEST

(75) Inventors: Satoshi Hara; Toshio Kusumi, both of Osaka (JP)

(73) Assignee: Daikin Industries Ltd., Osaka-fu (JP)

( * ) Notice: Subject to any disclaimer, the term of this patent is extended or adjusted under 35 U.S.C. 154(b) by 0 days.

(21) Appl. No.: 09/303,685

(22) Filed: May 3, 1999

(30) Foreign Application Priority Data

Mar. 19, 1999 (JP) .................................................. 11-075829
Apr. 21, 1999 (JP) .................................................. 11-113600

(51) Int. Cl.$^7$ .............................. G01M 3/20; B29C 9/00; G01N 15/08; B01D 23/00
(52) U.S. Cl. .................................. 73/38; 73/40.7; 55/423; 55/479; 264/9; 264/12
(58) Field of Search ................................. 73/38, 40.7, 40; 55/423, 431, 479, 385.2; 264/9–15

(56) References Cited

U.S. PATENT DOCUMENTS

| | | | |
|---|---|---|---|
| 2,072,872 | * | 3/1937 | Finkelstein ................................. 73/51 |
| 2,819,608 | * | 1/1958 | McLaren et al. ......................... 73/38 |
| 2,833,140 | * | 5/1958 | Austen et al. .............................. 73/38 |
| 4,382,378 | * | 5/1983 | Wadsworth et al. ...................... 73/38 |
| 4,402,214 | * | 9/1983 | Morgan et al. .......................... 73/40.7 |
| 4,686,848 | * | 8/1987 | Casselberry et al. ..................... 73/38 |
| 4,875,360 | * | 10/1989 | Ziemer ................................... 73/40.7 |
| 5,001,463 | * | 3/1991 | Hamburger ........................... 340/627 |
| 5,073,482 | * | 12/1991 | Goldstein ................................ 435/5 |
| 5,203,201 | * | 4/1993 | Gogins ..................................... 73/38 |
| 5,351,523 | * | 10/1994 | Blackford et al. ........................ 73/38 |
| 5,361,625 | * | 11/1994 | Ylvisaker ................................. 73/38 |
| 5,438,861 | * | 8/1995 | Sisbarro et al. .......................... 73/40 |
| 5,563,334 | * | 10/1996 | Bracht et al. ............................. 73/38 |
| 5,736,073 | * | 4/1998 | Wadley et al. . | |

FOREIGN PATENT DOCUMENTS

| | | |
|---|---|---|
| 5-317690 | 12/1993 | (JP) . |
| 8-136437 | 5/1996 | (JP) . |

\* cited by examiner

Primary Examiner—Hezron Williams
Assistant Examiner—David J. Wiggins
(74) Attorney, Agent, or Firm—Birch, Stewart, Kolasch & Birch, LLP

(57) ABSTRACT

The present invention provides a novel group of particles for air filter inspection which solves problems caused by volatilization and scattering of those particles at the downstream side of the air filter in use, enables an air filter inspection with superior stability and reproducibility, and may be produced by using a comparative inexpensive manufacturing device, and manufacturing methods as well as inspection methods of such a group of particles.

The group of particles for air filter inspection consists of a plurality of aggregate particles having a particle size of not less than 0.1 $\mu$m, each aggregate particle being constituted by solid primary particles having an average particle size of less than 55 nm. Further, the inspection method for an air filter has the steps of: producing the group of particles by atomizing and drying a suspension containing the solid primary particles having the average particle size of less than 55 nm, introducing the group of particles into the upstream side of the air filter, and detecting any of the group of particles leaked out of the downstream side of the air filter with a particle detector.

23 Claims, 5 Drawing Sheets

(a)    (b)

GROUP OF PARTICLES FOR AIR FILTER TEST AND METHOD OF AIR FILTER TEST

BACKGROUND OF THE INVENTION

1. Field of the Invention

The present invention relates to a novel group of particles used for air-filter inspection (test), and more particularly to, for example, a group of particles used for inspecting an air filter for use in clean rooms and an inspection method for air filters using such a group of particles.

2. Description of the Related Art

Elimination of dusts in the air is normally carried out by making the air pass through an air filter. In particular, in order to eliminate dusts from a clean room, an air filter with high performance, such as an high efficiency partyiulate air filter (HEPA), and a ultra low penetration air filter (ULPA), which can capture not less than 99.97% of fine particles having a particle size of 0.3 $\mu$m, is used, and these fine particles inside the clean room are constantly eliminated so that a predetermined degree of cleanliness is maintained in the clean room. When there is any leakage in the above mentioned high-performance air filter, such as a leakage due to a pin hole in the filter material or a leakage in a connecting section between the air filter and the frame, it may exert a serious influence upon the degree of cleanliness of the clean room, therefore, all the high performance air filters to be used are actually subjected to an inspection for any leak or reduction in its performance.

Here, in the present specification, "inspection" includes various inspecting operations for any leakage in the air filter or for air-filter performances. These inspecting operations are conducted as follows:

While airflow is made to direct to an air filter, a group of particles used for filter inspection or an aerosol including such particles is supplied to the airflow at the upstream side of the filter, and the group of the particles leaked out of the filter is detected at the downstream side of the filter by using, for example, a particle measuring device.

In general, a group of particles of a liquid organic compound having a low vapor pressure, such as dioctyl phthalate (DOP), stearic acid, dioctyl sebacate (DOS) and paraffin oil are used as a group of particles for filter inspection as standardized in JIS Z 8901. The group of the above particles is generated by an aerosol generator using a vapor condensing method or a pressurized atomization method.

However, when a group of these particles is used to inspect the above mentioned high performance air filters, a problem arises in which, in spite of its low vapor pressure, the organic compound vaporizes from a small quantity of particles that were captured by the filter material of the air filter and adhere thereto. Therefore, when an air filter which has been subjected to the inspection by using such a group of particles is installed in a clean room for semiconductors, the adhering organic compound may volatilize and scatter and its vapor may outflow from the air filter to the downstream side, and adheres onto, for example, silicon wafers, thereby adverse effects on the wettability and electrical characteristics of the silicon wafers, and consequently a reduction in the yield of the semiconductors may be caused. Additionally, with respect to DOP, its possibility of causing cancers has been conventionally pointed out, and recently, its harmfulness as an endocrine disrupter is pointed out.

For these reasons, a group of particles, made of solid substances which is inherently free from evaporation and outflowing, has been researched and developed.

For example, a method in which dusts in the air are used has been known; however, since the size, shape and concentration, for example, of dust particles are not uniform, it is difficult to carry out inspections stably with high reproducibility. Moreover, when the concentration of dusts in the air is low, it takes a long time to carry out the inspection, and there is a possibility such a method fails to find out leakage. Furthermore, since dusts in the air may contain heavy metals, etc., it is not preferable to allow them to adhere to the air filter.

Moreover, Japanese Patent Kokai Publication No. 317690/1993 (Tokukaihei 5-317690) discloses a aggregate particles, as a group of particle for filter inspection, which is obtained through atomizing a suspension of polystyrene latex (PSL) particles that are solid particles having a known particle size and a globular shape, pulverizing the generated liquid droplets and drying the droplets. However, since the PSL particles easily coagulate in a dispersant, it is difficult to prepare a suspension with a high concentration. Therefore, in order to obtain a particle concentration of the PSL particles necessary to function as particles used for air filter inspection, a device having a complicated and special mechanism is required; consequently, this method fails to easily provide aerosol having a sufficient concentration.

Furthermore, Japanese Patent Kokai Publication No. 136437/1996 (Tokukaihei 8-136437) discloses an inspection method for air filters in which: a suspension of silica particles having particle size ranging from 0.055 to 0.18 $\mu$m is atomized and dried, and the resulting silica particles having a particle size of not less than 0.1 $\mu$m are used. However, the silica particles obtained in this method have extremely deviated shapes from a globular shape in particles having a particle size in the vicinity of 0.1 $\mu$m to be used for inspection, and these particles have uneven surfaces with many protrusions and recesses (hereinafter, referred to as "irregular shape"). And the following problems may be caused.

With respect to a particle counter used for filter inspection, a light-scattering-type automatic particle counter (LPC) is generally used since it allows a simple measuring operation and continuous automatic driving, and provides the results of a measurement at once. In the measurement using the LPC, the particle size is measured by detecting the intensity of scattered light that is caused by scattering of radiated laser beam by the particles to be measured, and the particle size is normally obtained as a size corresponding to the true globe of a PSL particle. When the particles have irregular shapes, the scattered light varies depending on changes in the orientation of the particles to the laser light beam; consequently, there may be a great error in the obtained particle size. Therefore, it is difficult to measure the particle size stably with high reproducibility and also to correct the obtained particle size.

Moreover, when the particles have irregular shapes, fluid resistance that the particles undergo varies depending on the orientation of the particles to the fluid flow; therefore, the particle size that is obtained by using the LPC is not always consistent with the particle size that is subjected to fluid resistance in a gas flow (hereinafter, referred to as "aerodynamic particle size"). It is known through experiment that an aggregate in a lump shape with constituent particles of around 10 may undergo a fluid resistance 1.23 times larger than a globe having substantially the same size. Even though the difference between these two particle sizes is in the order of 0.01 $\mu$m, it will give a serious adverse effect on the reliability of the filter inspection; and in particular, in the case of high performance air filters such as HEPA and ULPA, the capturing efficiencies of the filter may differ by an order of magnitude in such an error range.

SUMMARY OF THE INVENTION

The present invention is aimed to provide a novel group of particles which mitigates the problems caused by the volatilization and scattering of the substances on the downstream side of the air filter when it is used, which substances had been adhered to an air filter material upon inspection of the air filter, enable an air filter inspection with superior stability and reproducibility and may be manufactured by using a comparatively inexpensive manufacturing device and a manufacturing method thereof, and also to provide a highly reliable inspection method for air filters which is achieved by using such particles for air filter inspection.

One aspect of the present invention is to provide a group of particles for air filter inspection which are preferably provided in aerosol form and constituted by a plurality of aggregate particles, each containing a plurality of solid primary particles having an average particle size of less than 55 nm.

In the context of the present invention, the term "aggregate particle" means, for example, a particle which is formed through physical aggregation of solid primary particles with each other due to their inherent characteristic, that is, a so-called secondary particle. The aggregate particle includes, for example, aggregated primary particles obtained by atomizing and drying a suspension including the primary particles.

In one embodiment of the group of particles of the present invention, each primary particle preferably has a particle size of less than 55 nm. In this case, since no primary particles having a particle size of not less than 55 nm substantially exist, the irregularity in the shape of the aggregate particles could be further mitigated.

In another embodiment, the group of particles of the present invention preferably has an average particle size of the primary particles less than 20 nm. In this case, since the shape of the primary particles becomes smaller as a whole, the irregularity in the shape of the aggregate particles may be further mitigated. In particular, each primary particle preferably has the particle size of less than 20 nm, and in this case, since no primary particles having a particle size of not less than 20 nm substantially exist, the irregularity in the shape of the aggregate particles may be furthermore mitigated.

The aggregate particle, which is obtained by using primary particles having various preferable particle sizes as described above, has a particle size of at least 0.1 $\mu$m in one preferred embodiment. In particular, when the primary particles having a particle size or an average particle size of less than 20 nm is used, the aggregate particle has a particle size of at least 0.055 $\mu$m. These aggregate particles are preferably used for air filter inspection as will be described later.

Here, in the present invention, the term "a group of particles" means a state in which a plurality of primary particles and/or secondary particles exist, which may be, for example, a group comprising the primary particles themselves and aggregate particles formed through aggregation of primary particles. Since a group of particles normally exist in a gas, it may be provided in aerosol form.

The group of particles of the present invention may contain aggregate particles and/or unaggregated solid primary particles having a particle size further smaller than that of the above mentioned aggregate particles as long as they do not cause adverse effects on the inspection. In particular, when the group of particles of the present invention are produced by a manufacturing method as will be described later, there is a possibility that the particles having such a smaller size may be included therein. However, such smaller particles may be generally used for air filter inspection without being eliminated through a particular treatment.

In the present invention, the term "average particle size" means a statistical number-average value of particle sizes, and the term "particle size" means a value measured by the a dynamic light scattering method as to solid primary particles, and means a value measured by the use of an electric mobility classification method as to aggregate particles that were constituted by aggregating primary particles.

BRIEF DESCRIPTION OF THE DRAWINGS

FIG. 6a depicts a primary particle size of 0.055 $\mu$m and FIG. 6b depicts a primary particle size of 0.01 $\mu$m.

Figure 1:
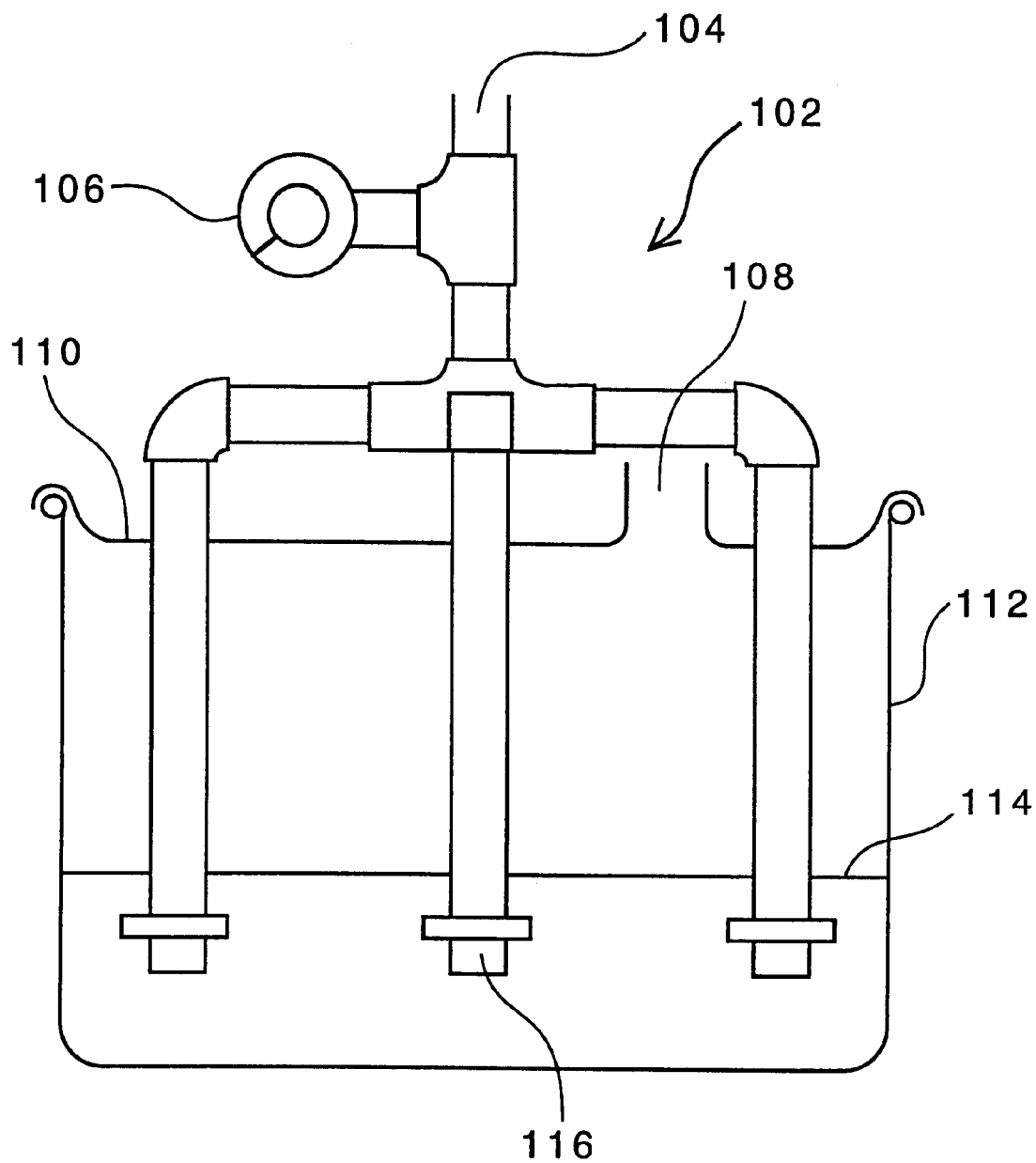
FIG. 1 is a chematic view of a particle generator of a Laskin nozzle type.

In the Figures, reference numerals represent the following elements, respectively: 102 . . . Laskin nozzle type particle generator; 104 . . . compressed air inlet; 106 . . . pressure gauze; 108 . . . discharging outlet; 110 . . . lid; 112. . . container; 114 . . . particle suspension; 116 . . . Laskin nozzle; 202. . . air compressor; 204. . . air dryer; 206 . . . regulator; 208 . . . filter; 210. . . dispersing dryer; 212 . . . americium-241; 214 . . . electrostatic classifier; 216 . . . filter; 218 . . . filter; 220. . . valve; 224 . . . condensation nucleus counter; 302 . . . americium-241; 304 . . . electrostatic classifier; 306 . . . filter; 308 . . . filter; 310 . . . valve; 312 . . . light-scattering-type automatic particle counter; and 314 . . . wave-height analyzer.

DETAILED DESCRIPTION OF THE INVENTION

Amazingly, the inventors have found that a group of particles, which include aggregate particles having a particle size of not less than 0.1 $\mu$m, and more preferably not less than 0.055 $\mu$m, and are constituted by a plurality of solid primary particles having an average particle size of less than 55 nm, more preferably having a particle size of less than 55 nm or an average particle size of 20 nm, and most preferably having a particle size of less than 20 nm, can be effectively used for air filter inspection, that the application of such a group of particles makes it possible to mitigate problems caused by volatilization and scattering of particles that adhere to an air filter after the air filter inspection, when the air filter is used, and to carry out an air filter inspection with better stability and reproducibility, and that such a group of particles may be produced by using a comparatively inexpensive manufacturing device; thus, the present invention has been devised.

Therefore, one feature of the present invention is that even when solid primary particles, which have a particle size smaller than that of silica particles disclosed in Japanese Patent Kokai Publication No. 136437/1996 (Tokukaihei 8-136437), are used to form aggregate particles that form a group of particles, an air filter inspection can be advantageously carried out by using such a group of particles.

Figure 6:
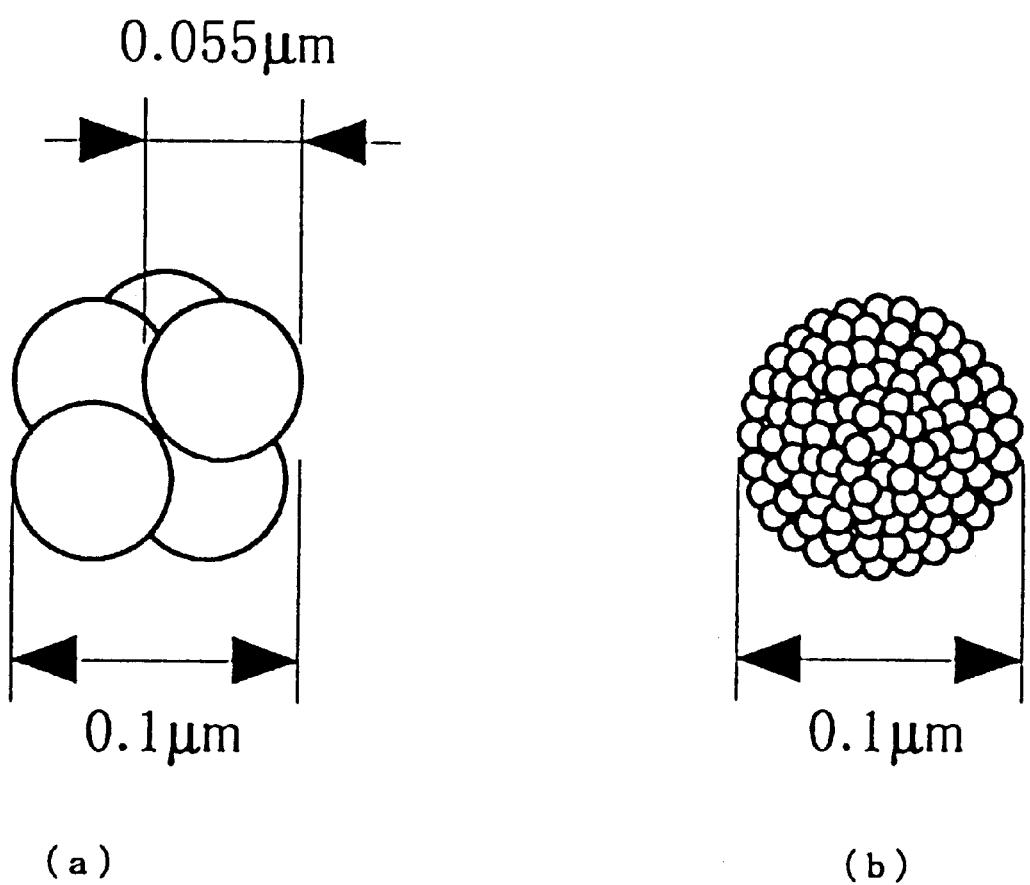
FIG. 6 is a schematic view of aggregate particles having an average particle size of 0.1 $\mu$m formed by the aggregation of the primary particles, where

With respect to aggregate particles having an major axis size of 0.1 μm formed by aggregating primary particles, FIG. 6 shows how the particle size of the primary particles give affects on the shape of the aggregate particles.

FIG. 6(a) shows a case in which the particle size of the primary particles is 0.055 μm, that is, approximately half the particle size of the aggregate particles, and in which aggregate particle is constituted by 6 primary particles. FIG. 6(b) shows a case in which the particle size of the primary particles is 0.01 μm, that is, 1/10 of the particle size of the aggregate particles, and in which an aggregate particle is constituted by approximately 1000 of the primary particles.

The particle shown in FIG. 6(a) is more irregular in its shape than that shown in FIG. 6(b) (that is, more different from the globular shape). Here, with respect to the major-minor axis ratio, that of FIG. 6(a) is approximately 2, and that of FIG. 6(b) is approximately 1.

Therefore, it may be understood that the smaller the average particle size of the primary particles which are to constitute each aggregate particle as compared with the particle size of the aggregate particles, the less irregular the shape of the resulting aggregate particles, thereby becoming closer to the globular shape. Therefore, the present invention uses primary particles having smaller sizes to form the group of particles as compared with the method disclosed in Japanese Patent Kokai Publication No. 136437/1996 (Tokukaihei 8-136437), therefore, applying such a group to an air filter inspection makes it possible to carry out a stable inspection with high reproducibility.

In the present invention, the primary particles mentioned above preferably have an average particle size or particle size of less than 55 nm, more preferably not more than 45 nm, further not more than 30 nm, most preferably not more than 20 nm, and in particular not more than 10 nm. The lower limit of the average particle size or the particle size is not particularly limited as long as no adverse effect is given on the inspection, and normally, even a particle size as small as the measurement limitation (approximately 1 nm) is applicable.

In the present invention, the range of the particle size of the aggregate particles contained in a group of particles to be formed is appropriately selected depending on performances of a filter to be inspected; and in the case of an inspection for a high performance filter such as an HEPA filter and a ULPA filter, it is normally set at not less than 0.050 μm, more preferably not less than 0.055 μm, most preferably in the range of 0.055 to 1 μm, and in particular in the range of 0.055 to 0.5 μm. Here, larger aggregate particles may of course be included as long as no adverse effect is given on the air filter inspection.

In one embodiment of the present invention, a group of particles for air filter inspection, which include aggregate particles having a major-minor axis ratio (a rate of major axis length to minor axis length) within the range of 1.0 to 1.4, and preferably 1.0 to 1.1 are provided. Such a group of particles can be easily obtained by using primary particles having an average particle size or a particle size of less than 20 nm, and in particular, of less than 10 nm.

In the context of the present invention, the term "major-minor axis ratio" means an index showing the shape of a particle, which is a value obtained by dividing the major axis length of a particle by the minor axis length of the particle (major axis length/minor axis length). In other words, when a particle is placed on a horizontal plane stably, this is given by a ratio of the length of the long side and the length of the short side of a minimum rectangle that circumscribes the particle's figure projected on the horizontal plane. Additionally, the shape of the solid primary particles is not particularly limited, as long as it does not give adverse effects on the formation of the aggregate particles, however, a shape similar to a globular shape is preferred.

As described in the above referring to FIG. 6, when the particle size of the primary particles constituting the aggregate particles is close to the particle size of the aggregate particles, the number of the primary particles constituting each aggregate particle is extremely restricted to several number level, therefore, it is more likely that the shape of the aggregate particles naturally assumes an irregular shape with extreme protrusions and recesses. However, it has been unexpectedly revealed that even when primary particles having a comparatively small particle size or average particle size of less than 55 μm are used as described earlier, the resulting aggregate particles can be effectively used for air filter inspection.

Moreover, when the particle size of the primary particles is made further smaller, the aggregate particles can be constituted by primary particles having a smaller particle size as compared with the particle size of the aggregate particles, and in this case, it is possible to further improve the irregularity of the aggregate particles. From such a point of view, in the group of particles of the present invention, the ratio of the average particle size of the primary particles constituting the aggregate particles to the particle size of the aggregate particles (the average particle size of the primary particles/the particle size of the aggregate particles) is preferably set in the range of 1/100 to 55/100, more preferably 1/100 to 40/100, and most preferably 1/100 to 30/100 and in the manufacturing method of a group of particles according to the present invention as will be described later, aggregate particles having a particle size within the above mentioned range can be obtained depending on the average particle sizes of the primary particles to be used.

In the present embodiment, the shape of the aggregate particles contained in a group of particles is improved in its irregularity, and in a more preferred embodiment, it is possible to provide a group of particles for filter inspection which allow a superior inspection by its stability and reproducibility since the shape of the aggregate particles is closer to the globular shape.

Since each of the aggregate particles of the present invention is constituted by the solid primary particles, the material of the aggregate particles is substantially the same as that of the solid primary particles. Thus, the application of the solid primary particles of this type makes it possible to solve problems caused by use of a group of liquid particles. With respect to the solid primary particles, those non-volatile solid particles which are superior in dispersing property without being dissolved in a dispersing medium, and has an average particle size of less than 55 nm may be used, whether they are made of an organic substance or an inorganic substance. For example, silica, titanium dioxide, alumina, etc. are preferably used; and silica is more preferably among them.

These solid primary particles may be prepared by using any known method; however, commercially available products may be adopted as long as they are appropriate for the primary particles of the present invention.

For example, silica is commercially available from Nippon Aerosol K.K. under the trade name AEROSIL. Titanium dioxide is commercially available from Nippon Aerosol K.K. under the trade name "Titanium dioxide" and alumina is commercially available from Nippon Aerosol K.K. under the trade name "Aluminum oxide C".

The above mentioned group of particles containing the aggregate particles of the present invention can be manufactured by atomizing a suspension containing solid primary particles having the above mentioned particle size, for example, the solid primary particles having an average particle size or a particle size of less than 55 nm, followed by drying them. Upon manufacturing the group of particles, the viscosity of the above mentioned suspension is selectable so as to efficiently obtain the group of particles preferably containing the target aggregate particles with a high concentration. The viscosity is preferably set at not more than 50 mPa·s, more preferably in the range of 1 to 50 mPa·s, and most preferably in the range of 1 to 10 mPa·s.

The medium used for the suspension of the primary particles is mainly water, such as industrial water, city water, distilled water, ion exchange water and ultra pure water; however, other media, such as lower alcohol, acetone, and water containing these may be used as long as it allows appropriate dispersion of the primary particles. Normally, in order to prevent impurities from being mixed in the aggregate particles, water from which impurities have been removed, such as ultra pure water, is preferably used.

The suspension may be prepared by adding a predetermined quantity of the primary particles to the above mentioned medium and mixing thereof sufficiently. At this time, a mixing means that is normally used, such as a magnetic stirrer, a stirrer, a shaking device and an supersonic washer, may be adopted.

The viscosity of the suspension may be adjusted by adjusting the concentration of the solid primary particles in the suspension, the average particle size of the primary particles, the kind of the solvent, the mixing ratio in the case of a mixed solvent and the temperature, etc.

The suspension of this type may be prepared by using any of conventional methods; however, commercially available products may be adopted as long as they are suitable for the suspension of the present invention.

With respect to silica, the following products are commercially available: brand name "Snowtex" available from Nissan Chemical Industries, Ltd., brand name "Cataloid-S" available from Shokubai Kasei Kogyo K.K. (Catalysts and Chemicals Ind. Co. Ltd.) and brand name "Adelite AT" available from Asahi Denka Kogyo K.K.

With respect to "atomizing means", the following atomizing means that were normally and conventionally used can be adopted: for example, a Collison atomizer, a Laskin nozzle type particle generator, a supersonic neblizer, etc.

With respect to "gas used for atomizing", it is not particularly limited, as long as it gives no adverse effect on the solid primary particles and the aggregate particles, etc. For example, air, nitrogen gas, argon gas, etc. may be used.

Moreover, with respect to "drying means", drying means which was normally conventionally used is applicable. For example, a gas flow dryer, a dispersing dryer, etc., in which a dry gas is mixed with aerosol after having been atomized, may be used.

In preparation of the group of particles according to the present invention, since gas is used for atomizing or drying optionally, the group of particles is formed in a condition in which it is contained in a gas. Therefore, the resulting group of particles is in an aerosol condition when it is not separated from the gas. Therefore, the present invention also provides aerosol used for air filter inspection, which is constituted by the above mentioned group of particles of the present invention and the gas.

In the present invention, with respect to "the gas" constituting the aerosol, the gas used for atomizing the suspension may be used as it is, or the gas used for drying the suspension may be used as it is, or both of the gases may be used at the same time. These gases are not particularly limited, as long as they give no adverse effects on the group of particles and an air filter, etc. to be inspected by using the particles. For example, air, nitrogen gas, argon gas, etc. are preferably used; and air is particularly preferable.

The aerosol may also be prepared by using the group of particles prepared by atomizing and drying the suspension as it is, for example, without separating the group of particles from the gas using, for example, a filter or adding the above mentioned gas or removing the existing gas, in order to adjust the concentration, etc. of the group of particles as necessarily.

In another aspect of the present invention, an inspection method for an air filter is provided in which: the group of particles of the present invention obtained as described above are generated, the group of the particles thus generated are introduced into the upstream side of the air filter, and any of the group of particles leaked out of the downstream side of the air filter are detected by using a particle detector.

For example, an inspection method for an air filter is provided, in which: a suspension containing solid primary particles having an average particle size of less than 55 nm is atomized and dried so that a group of particles containing a plurality of aggregate particles are generated, the group of the particles thus generated are introduced into the upstream side of the air filter, and any of the group of particles leaked out of the downstream side of the air filter are detected by using a particle detector. The aggregate particles contained in the group of particles thus generated have a particle size of not less than 0.1 $\mu$m and more preferably not less than 0.055 $\mu$m.

The group of particles obtained by atomizing and drying the above mentioned suspension of the primary particles, as it is, can be supplied into the upstream side of the air filter as aerosol so as to carry out an inspection for the air filter.

The detection of the group of particles on the downstream side of the air filter can be carried out by a normally used detection method for particles and/or detector. For example, a condensation nucleus counter, a light-scattering-type automatic particle counter (LPC), a photometer, etc. can be used for the detection; and, in particular, a light-scattering-type automatic particle counter (LPC) is preferably used.

In the inspection method of the present invention, the features of the group of particles for inspection and the manufacturing method thereof mentioned above may be applied, and for example, the primary particles preferably have an average particle size or a particle size at less than 55 nm, more preferably not more than 45 nm, far more preferably not more than 30 nm, the most preferably not more than 20 nm, and by far the most preferably not more than 10 nm.

Moreover, the viscosity of the suspension of the primary particles is preferably set at not more than 50 mPa·s, more preferably in the range of 1 to 50 mPa·s, and most preferably in the range of 1 to 10 mPa·s.

In the present inspection method, it is preferable to generate aerosol which contains aggregate particles having a particle size of not less than 0.055 μm at a concentration of preferably not less than $3.5 \times 10^3$ particles/cm$^3$, more preferably not less than $3.5 \times 10^4$ particles/cm$^3$, and most preferably not less than $3.5 \times 10^5$ particles/cm$^3$. Here, the higher the concentration of the aggregate particles introduced into the gas flow at the upstream side of the filter, the more preferable because it ensures the detection for leak more positively.

The concentration of the aggregate particles to be generated is appropriately selected depending on air filters to be inspected. The above mentioned concentration of not less than $3.5 \times 10^3$ particles/cm$^3$ is suitable for air filters, such as HEPA filters or ULPA filters.

In the inspection method for air filters of the present invention, silica particles are preferably used as the solid primary particles.

For example, in the above mentioned inspection method, when aggregate particles having a particle size of not less than 0.055 μm, and more preferably in the range of 0.055 to 0.5 μm are generated at a concentration of not less than $3.5 \times 10^3$ particles/cm$^3$, the primary particles in the suspension has an average particle size in the range of 1 to 20 nm, and more preferably in the range of 1 to 10 nm, and the suspension of the silica primary particles has a viscosity in the range of 1 to 50 mPa·s, and more preferably in the range of 1 to 10 mPa·s.

The inspection method of the present invention can be applied to inspections for various air filters. For example, the following air filters are listed by way of example; air filters for clean room used for medical and biological fields, air filters for masks, air filters for gas lines, and air filters for manufacturing devices of disks (such as floppy disks, optical disks, MiniDisks, compact disks, magneto-optic disks, digital audio disks and hard disks). In particular, it is suitable for air filter inspection for clean rooms used for manufacturing electric and electronic devices.

EXAMPLES

The following Example and Comparative Examples are provided to further illustrate the present invention concretely and precisely. These Example and Comparative Examples show merely embodiments of the present invention and should not be construed as limiting the scope of the present invention.

Example 1

(1) Preparation of a group of particles containing aggregate particles

A suspension is prepared by using commercially available colloidal silica (ST-OXS (brand name) available from Nissan Chemical Industries, Ltd.) having an average particle size of 6 nm, a solid-component concentration of 10.6 percent by weight and a viscosity of not more than 1.2 mPa·s as solid primary particles, and this suspension is atomized by using a Laskin nozzle type particle generator (the diameter of the spout 1 mm in the specification of the nozzle) and clean air having a pressure of 2 kgf/cm2 ; thus, fine droplets containing silica are generated.

When the suspension to be atomized is prepared, a dispersion medium, for example, pure water (distilled water, etc.) may be used for dilution. However, since the colloidal silica has such a low viscosity of not more than 1.2 mPa·s in spite of having the relatively high solid-component concentration of 10.6 percent by weight, there is no need to use the solvent such as pure water (distilled water) and the suspension was atomized without causing plugging in the atomizing spout. The fine droplets containing silica thus generated were dried in an airflow so that a group of particles (in the form of aerosol in this case) containing aggregate particles formed by aggregating primary particles of silica was obtained.

(2) Measurements of the distribution and the number of particles of aggregate particles The obtained aggregate particles were classified by using an electrostatic classifier which will be described later, and the number of the aggregate particles were measured by using a condensation nucleus counter; thus, the particle size distribution was determined. According to this distribution, the concentration in the gas of the aggregate particles having a particle size of not less than 0.05 μm was $7.1 \times 10^6$ particles/cm$^3$ This concentration of the aggregate particles is close to the upper limit value that can be achieved by a simple atomizing method, and is a sufficient concentration for carrying out a filter inspection.

(3) Measurements of the shape of aggregate particles

Figure 4:
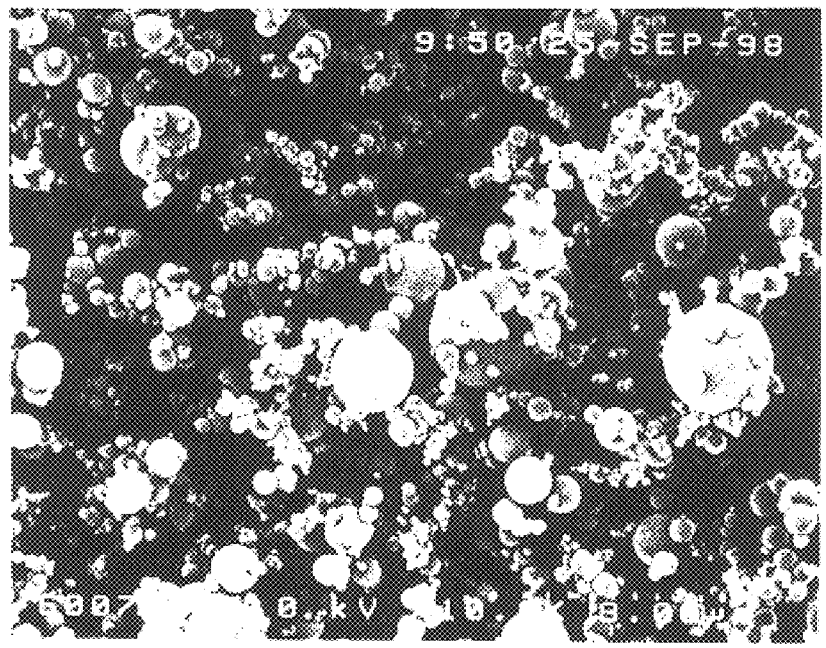
FIG. 4 is an electron micrograph showing a structure of the aggregate particles in which silica (average particle size: 6 nm) is used as solid primary particles.
Figure 5:
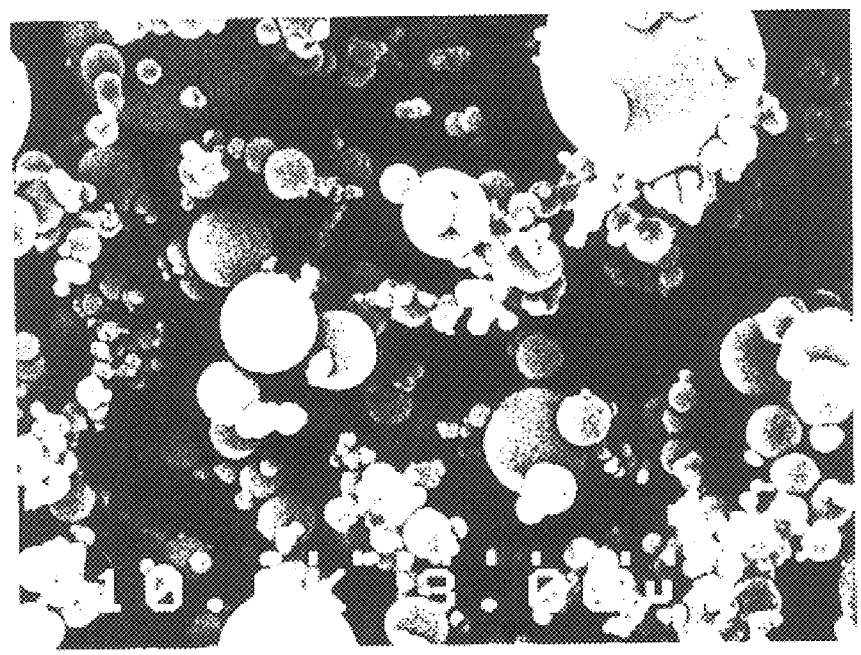
FIG. 5 is an electron micrograph showing a structure of the aggregate particles in which silica (average particle size: 6 nm) is used as solid primary particles.

The shape of the aggregate particles was measured by using an electronic microscope. FIGS. 4 and 5 show the structure of the aggregate particles observed. FIG. 4 is a photomicrograph of a magnification of 10000 times by using a voltage of 4.0 kV. FIG. 5 is a partially enlarged view of FIG. 4. It was observed that aggregate particles whose particle size is approximately not less than 0.1 μm have shapes very close to the globular shape. It is confirmed that the surface of those aggregate particles is extremely less susceptible to protrusions and recesses. The average major-minor axis ratio of the aggregate particles was 1.0, and it is found that the shape of the aggregate particles of the present invention is very close to the globular shape.

(4) Manufacturing device of a group of particles containing aggregate particles and evaluation method for the group of particles containing the aggregate particles (a) Manufacturing device of a group of particles containing aggregate particles and method for measuring the particle size and concentration A Laskin nozzle type particle generator (102), used for generating the fine droplets by atomization, is shown in FIG. 1 as its schematic view.

In the Laskin nozzle type particle generator (102) of FIG. 1, a container (112) is sealed by a lid (110), and compressed air is introduced therein through a compressed air inlet (104) from another device, with the result that air having a pressure displayed on a pressure gauge (106) is allowed to flow into a suspension (114) contained in the container from a Laskin nozzles (116). The compressed air, allowed to flow therein, can atomize the suspension in the form of foams. These foams form fine droplets containing particles in the container (112), and are discharged through a discharging outlet (108).

Other than the Laskin nozzle type particle generator (102), any of a Collison atomizer, a supersonic neblizer, etc. may be adopted.

Figure 2:
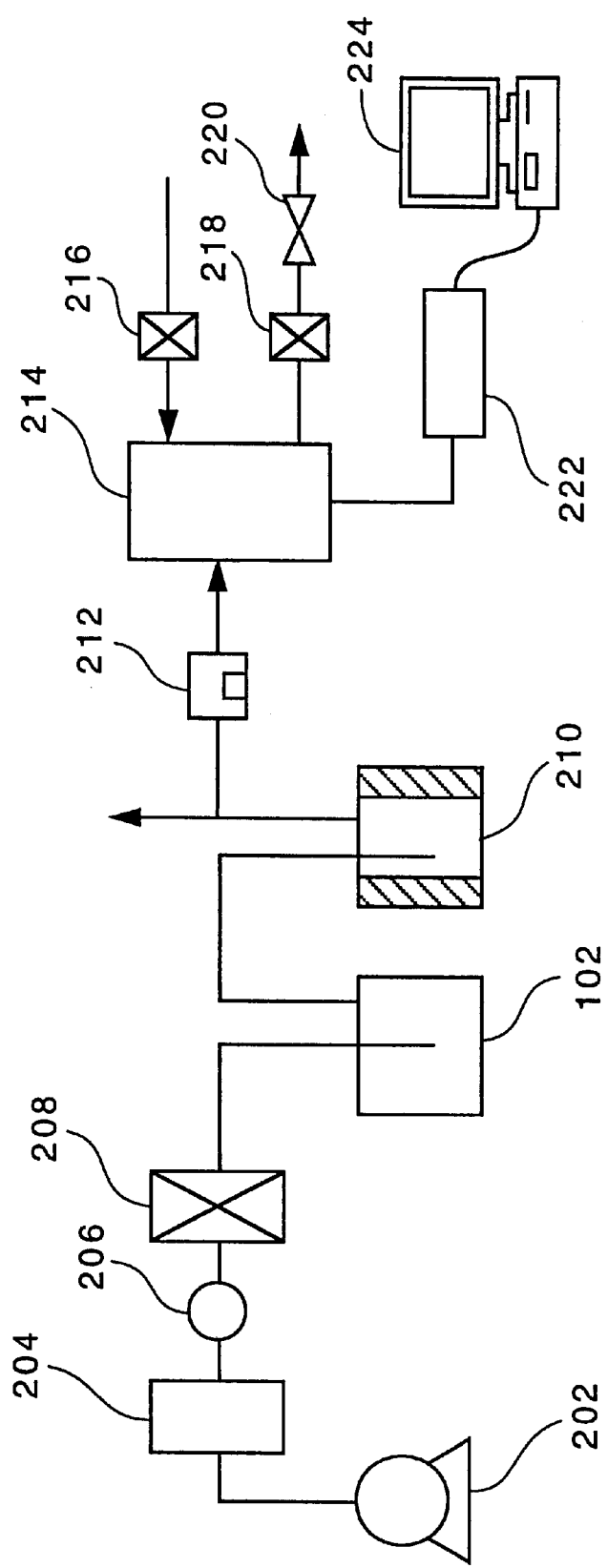
FIG. 2 is a schematic view of a device used for producing aggregate particles and for measuring the particle size and concentration of the aggregate particles.

FIG. 2 is a schematic view of a device used for generating a group of particles containing aggregate particles and for measuring the particle size and concentration of the aggregate particles, comprising (202), (204, 206) and (208) connected to the Laskin nozzle type particle generator (102); and a dispersing dryer (210), americium-241 (212), a filter (216), a filter (218), a valve (220), an electrostatic classifier (Model 3071A available from TSI) (214), a condensation nucleus counter (Model 3022A available from TSI) (222)

and a scanning-type mobility particle-size distribution measuring device (Model 3934 available from TSI) (224) including a personal computer. Such a device is well known.

The dispersing dryer (210) is provided with silica gel on the periphery part thereof so that the droplets are allowed to pass through the dispersing dryer (210), with the result that the droplets are dried; thus, a group of particles containing aggregate particles are obtained. The group of particles containing aggregate particles passes through americium-241 (212), and are classified by the electrostatic classifier (214) and subjected to measurements on the particle condensation by the condensation nucleus counter (222).

The results of the measurements are processed by the personal computer. The filters (208, 216 and 218) are used for preventing particles other than the measuring aggregate particles from entering the device, and when measurements are carried out on a group of particles containing aggregate particles for inspecting HEPA or ULPA filters for a clean room, it is preferable to use HEPA or ULPA filters as those filters. The americium-241 (212) is used for making the charged state of the group of particles containing the aggregate particles to those in an equilibrium state.

(b) Measurements on the shape and the major-minor axis ratio (major axis length/minor axis length) of aggregate particles.

The shape of aggregate particles were observed and the major-minor axis ratio (major axis length/minor axis length) were measured over observation of the shape of the aggregate particles captured by using filters, through a scanning-type electronic microscope. For example, the aggregate particles to be measured were captured by using a filter, for example, an HEPA filter, a ULPA filter or a membrane filter, etc. and a surface of the filter-material to which the aggregate particles had adhered was photographed with a magnification of 10000 times by using an electronic microscope. The photographed area covered a range of 5 $\mu$m×5 $\mu$m.

With respect to the measurements on the major-minor axis ratio, aggregate particles to be measured are arbitrarily selected within one viewing field, and the major-minor axis ratios were measured on the respective aggregate particles. The number of the aggregate particles to be measured is set to not less than 100, and the average value of the major-minor axis ratios thereof is defined as the major-minor axis ratio of the entire aggregate particles.

Comparative Examples 1 and 2

In order to examine effects of the major-minor axis ratio when a light-scattering-type automatic particle counter (LPC) is used for measuring the particle size of the group of particles containing aggregate particles, a group of particles constituted by aggregate particles having different major-minor axis ratios was prepared and their scattered light intensities were measured by using an LPC. (1) Preparation for a group of particles constituted by aggregate particles having different major-minor axis ratios and evaluation based on scattered light intensities thereof.

In Comparative Example 1, a suspension is prepared by using commercially available colloidal silica (Snowtex ST-ZL (brand name) available from Nissan Chemical Industries, Ltd.) having an average particle size of 87 nm, a solid-component concentration of 40.5 percent by weight and a viscosity of 2.6 mPa·s as solid primary particles, and this suspension is atomized by using a Laskin nozzle type particle generator (the diameter of the spout 1 mm in the specification of the nozzle) and clean air having a pressure of 2 kgf/cm$^2$; thus, fine droplets containing silica are generated. The fine droplets containing silica thus generated were dried in a gas flow so that a particle group having aggregate particles was obtained.

The resulting group of particles containing the aggregate particles was classified by using an electrostatic classifier, and the scattered light intensity was measured by a method as will be described later by using an LPC; thus, the distribution of scattered light intensities was obtained. Based upon the distribution, the scattered light intensity on the aggregate particles having a particle size of 0.2 $\mu$m was determined.

Moreover, with respect to the distribution of Example 1, the scattered light intensity on the aggregate particles having a particle size of 0.2 $\mu$m was obtained in the same manner as described above. Here, with respect to a single silica globular particle having a particle size of 0.2 $\mu$m, the estimated value in the LPC based upon Mie theory is shown in Table 1 as Comparative Example 2. Furthermore, the major-minor axis ratio of Comparative Example 1 was evaluated by the method described in Example 1 (4)(b).

The scattered light intensity of Example 1 is approximately two times the scattered light intensity of Comparative Example 1, and substantially equivalent to the scattered light intensity of Comparative Example 2. When the scattered light intensity of Comparative Example 2 is used as the standard, the particle size may be estimated at 0.190 $\mu$m according to the scattered light intensity of Example 1, and the particle size may be estimated at 0.175 pm according to the scattered light intensity of Comparative Example 1. Therefore, the error of the particle sizes is not more than 0.01 $\mu$m between Example 1 and Comparative Example 2; however, the error thereof between Comparative Example 1 and Comparative Example 2 is not less than 0.02 $\mu$m.

TABLE 1

| | Example | Comparative Example | |
|---|---|---|---|
| | 1 | 1 | 2 |
| Average Particle Size of Primary Particles (nm) | 6 | 87 | 200 |
| Scattered light Intensity (mV) | 4308 | 2700 | 5700a) |
| Major-minor axis ratio | 1.0 | 2.2 | 1.0 | a)Estimated values obtained by using the refractive index (1.48) of silica.

Figure 3:
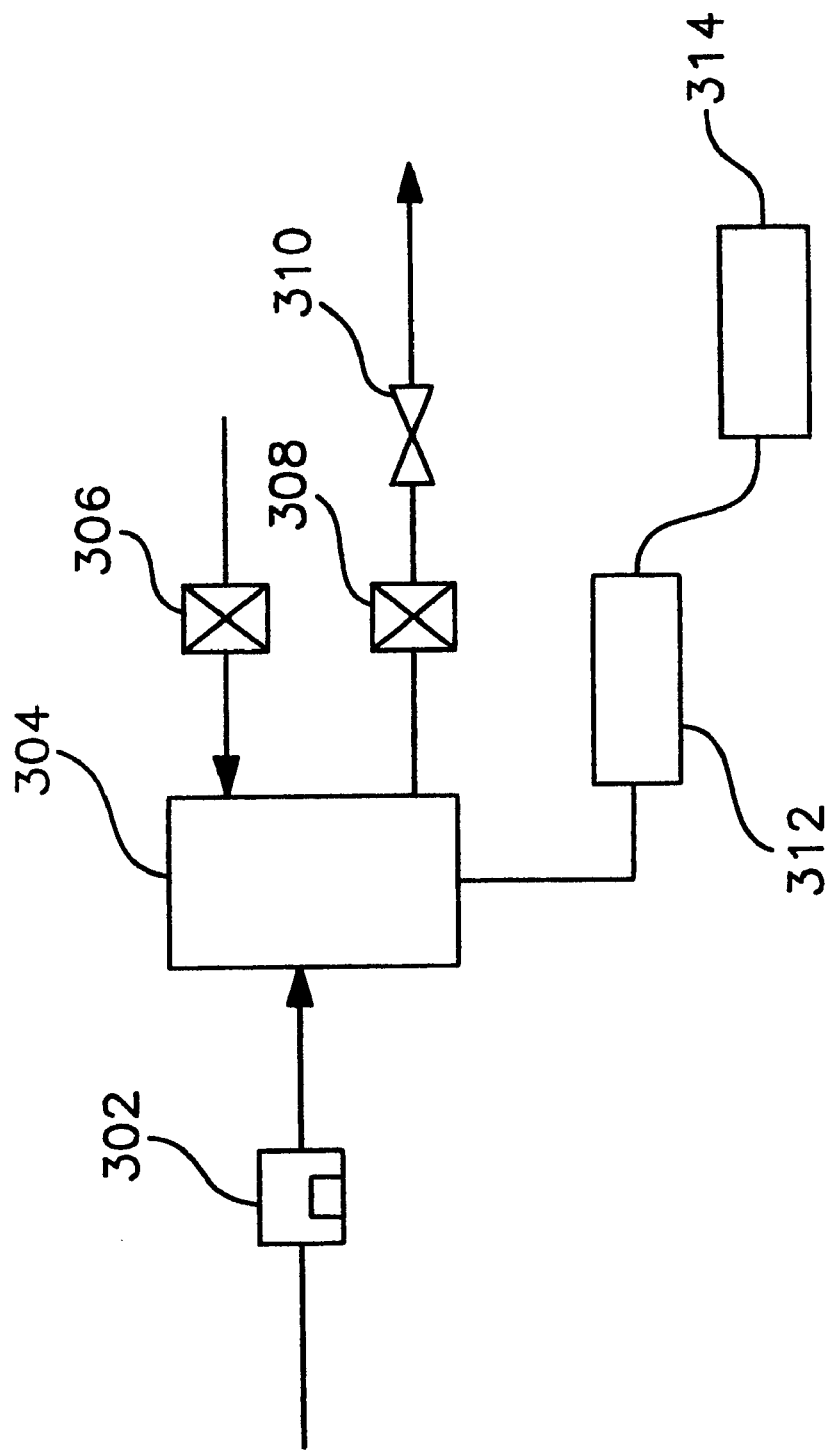
FIG. 3 is a schematic view of a device used for measuring the intensity of the scattered light from the aggregate particles.

(2) Measuring method of the scattered light intensity of a group of particles containing aggregate particles FIG. 3 is a schematic view of a device for measuring the scattered light intensity of aggregate particles. This device is constituted by americium-241 (302), filters (306, 308), a valve (310), differential mobility analyzer (304) of Model 3071A available from TSI for classifying multiple dispersed particles, an LPC (312) of KC-21 Type available from RION Co., Ltd. and a pulse-height analyzer (314) of KH-02A Type available from Leon Co., Ltd. The device of this type is conventionally known.

For example, a group of particles containing aggregated particles, which have been generated by the particle generator (102) such as that of Laskin nozzle type, the dispersing dryer (210), etc. as shown in FIGS. 1 and 2, is allowed to pass through the americium-241 (302), classified into particles whose particle sizes have already been known by the electrostatic classifier (304), and enter the LPC (312) at which it is subjected to measurements on the distribution of the scattered light intensity by the wave-height analyzer (314).

EFFECTS OF THE INVENTION

The aggregate particles constituting a group of particles used for air filter inspection of the present invention consist of a plurality of solid primary particles, and the average particle size of the primary particles is smaller than that of conventionally used particles; therefore, the group of particles used for air filter inspection of the present invention makes it possible to reduce problems by using the solid primary particles, which problem is that particles adhering to an air filter are volatilized and scattered when the air filter is used after inspection thereof, and to carry out an air filter inspection with better stability and reproducibility by generating aggregate particles which have become less susceptible to irregularities in their shape and have shapes preferably closer to the globe, with high density.

Moreover, in one embodiment of the aggregate particles constituting a group of particles for air filter inspection of the present invention, the aggregate particles are constituted by silica particles; therefore, in one embodiment of the group of particles for air filter inspection of the present invention, the raw material for the particles is easily obtained, and the group of particles can be manufactured by using a comparatively inexpensive manufacturing device, and further they are suitably used for an inspection for high performance air filters such as HEPA filters and ULPA filters.

Furthermore, in one embodiment of the air filter inspection method of the present invention, since the group of particles comprising aggregate particles having a particle size of not less than 0.055 $\mu$m at a concentration of not less than 3.5×10$^3$ particles/cm$^3$, which were produced by atomizing and drying a suspension containing solid primary particles having a viscosity of not more than 50 mPa·s, is used, the group of particles is suitably used for an inspection for high-performance air filters such as HEPA filters and ULPA filters.

What is claimed is:

1. A group of particles used for air filter inspection, comprising a plurality of aggregate particles constituted by a plurality of solid primary particles having an average particle size of less than 55 nm, wherein each of the aggregate particles has a major-minor axis ratio within a range of 1.0 to 1.4.

2. The group of particles used for air filter inspection according to claim 1, wherein each of the primary particles has a particle size of less than 55 nm.

3. The group of particles used for air filter inspection according to claim 1 or claim 2, wherein the primary particles have an average particle size of less than 20 nm.

4. The group of particles used for air filter inspection according to claim 1, wherein each of the primary particles has a particle size of less than 20 nm.

5. The group of particles used for air filter inspection according to claim 1, wherein each of the aggregate particles has a particle size of not less than 0.1 $\mu$m.

6. The group of particles used for air filter inspection according to claim 1, wherein each of the aggregate particles has a particle size of not less than 0.055 $\mu$m.

7. The group of particles according to claim 1, wherein the solid primary particles are silica particles.

8. The group of particles according to claim 1, which exists in an aerosol form.

9. The group of particles according to claim 1, comprising aggregate particles having a particle size of not less than 0.055 $\mu$m at a concentration of not less than 3.5×10$^3$ particles/cm$^3$.

10. The group of particles according to claim 1, further comprising aggregate particles and/or unaggregated solid primary particles having a particle size of less than 0.055 $\mu$m.

11. The group of particles according to claim 1 wherein each of the aggregate particles has a major-minor axis ratio within the range of 1.0 to 1.1.

12. An inspection method for an air filter comprising the steps of:

Generating a group of particles containing a plurality of aggregate particles each constituted by a plurality of solid primary particles by atomizing and drying a suspension containing the plurality of solid primary particles having an average particle size of less than 55 nm and each of the aggregate particles having a major-minor axis ratio within a range of 1.0 to 1.4; introducing the group of particles thus generated into an upstream side of said air filter; and detecting any of the group of particles which are leaked out of a downstream side of the air filter by using a particle detector.

13. The inspection method according to claim 12, wherein each of the primary particles has a particle size of less than 55 nm.

14. The inspection method according to claim 12 or claim 13, wherein the primary particles have an average particle size of less than 20 nm.

15. The inspection method according to claim 12, wherein each of the primary particles has a particle size of less than 20 nm.

16. The inspection method according to claim 12, wherein each of the aggregate particles has a particle size of not less than 0.1 $\mu$m.

17. The inspection method according to claim 12, wherein each of the aggregate particles has a particle size of not less than 0.055 $\mu$m.

18. The inspection method according to claim 12, wherein the solid primary particles are silica particles.

19. The inspection method according to claim 12, wherein the group of particles exists in an aerosol form.

20. The inspection method according to claim 12, comprising aggregate particles having a particle size of not less than 0.055 $\mu$m at a concentration of not less than 3.5×10$^3$ particles/cm$^3$.

21. The group of particles according to claim 12, further comprising aggregate particles and/or unaggregate solid primary particles having a particle size of less than 0.055 $\mu$m.

22. The inspection method according to claim 12, further comprising the step of atomizing a suspension having a viscosity of not more than 50 mPa·s.

23. The inspection method of claim 12 wherein each of the aggregate particles has a major-minor axis ratio within the range of 1.0 to 1.1.

* * * * *